United States Patent
Tiwald

(10) Patent No.: US 7,920,264 B1
(45) Date of Patent: Apr. 5, 2011

(54) HORIZONTAL ATTENUATED TOTAL REFLECTION SYSTEM

(75) Inventor: Thomas F. Tiwald, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 422 days.

(21) Appl. No.: 12/220,661

(22) Filed: Jul. 28, 2008

Related U.S. Application Data

(60) Continuation-in-part of application No. 11/880,427, filed on Jul. 23, 2007, now abandoned, which is a division of application No. 11/393,519, filed on Mar. 30, 2006, now Pat. No. 7,265,839.

(60) Provisional application No. 60/668,174, filed on Apr. 2, 2005.

(51) Int. Cl.
*G01J 4/00* (2006.01)

(52) U.S. Cl. ..................................................... 356/369
(58) Field of Classification Search ........... 356/369–370; 359/831, 833, 834
See application file for complete search history.

(56) References Cited

U.S. PATENT DOCUMENTS

| | | | | |
|---|---|---|---|---|
| 5,856,873 A * | 1/1999 | Naya et al. | .................... | 356/369 |
| 5,942,754 A | 8/1999 | Yamaguchi et al. | ..... | 250/339.12 |
| 5,943,136 A | 8/1999 | Pipino et al. | .................. | 356/440 |
| 6,084,675 A | 7/2000 | Herzinger et al. | ............ | 356/364 |

* cited by examiner

*Primary Examiner* — Tarifur Chowdhury
*Assistant Examiner* — Tara S Pajoohi
(74) *Attorney, Agent, or Firm* — James D. Welch

(57) ABSTRACT

Horizontally oriented attenuated total reflection (HATR) system applied in spectroscopic ellipsometer or polarimeter systems, and methodology of use.

4 Claims, 4 Drawing Sheets

HORIZONTAL ATTENUATED TOTAL REFLECTION SYSTEM

This application is a CIP of application Ser. No. 11/880,427 Filed Jul. 23, 2007, (now abandoned), which was a Divisional of application Ser. No. 11/393,519 Filed Mar. 30, 2006, (now U.S. Pat. No. 7,265,839), and therevia claims Benefit of Provisional Application Ser. No. 60/668,174 Filed Apr. 2, 2005.

TECHNICAL FIELD

The present invention relates to systems for use in practicing spectroscopic ellipsometry, and more particularly to a horizontally oriented attenuated total reflection system.

BACKGROUND

The practice of Attenuated Total Reflection (ATR) is known. Horizontal Attenuated Total Reflection (HATR) systems have been applied in Spectrophotometers, which measure the attenuation of electromagnetic beam intensity, for years. Further, vertically oriented liquid containing cells have been applied in Spectroscopic Ellipsometer Systems, which measure changes in Polarization State of a beam of electromagnetic beam radiation. This is reported, for instance, in a paper by the Inventor herein, titled "Determination of the Mid-IR Optical Constants of Water and Lubricants Using IR Ellipsometry Combined with an ATR Cell", Tiwald et al., Thin Solid Films, 313-314 (1998). In particular, said paper describes the application of Spectroscopic Ellipsometry using Infrared (IR) range wavelengths to investigate a liquid sample placed into a cell with a vertically elongated and oriented reservoir. Vertically oriented liquid containing cells for application in, for instance, Spectrophotometers and Spectroscopic Ellipsometry, are even found in the catalog of the Harrick Scientific Corporation.

With the present invention in mind the following prior art has been identified:
A patent to Herzinger U.S. Pat. No. 6,084,675 is disclosed as it comprises rotatably adjustable mirrors in a system, (ie. a compensator retarder), for application in spectroscopic ellipsometer and polarimeter systems. Patents to Pipino e al., U.S. Pat. No. 5,943,136 and Yamaguchi et al., U.S. Pat. No. 5,942,754 are disclosed as they were identified by the Examiner in a Parent Application.

What has not been known to the knowledge of the Inventor, is the application of Horizontal Attenuated Total Reflection (HATR) systems in Spectroscopic Ellipsometer and Polarimeter Systems. Need remains for convenient to apply (HATR) systems applied in Spectroscopic Ellipsometer and Polarimeter Systems. In particular, (HATR) systems need not comprise "cells per se.", which are required in vertically oriented systems, as liquid can be placed on a horizontal surface and remain in place without being confined in a cell.

DISCLOSURE OF THE INVENTION

A present invention method of investigating a fluid or solid sample can also be recited as comprising the steps of providing a source of spectroscopic electromagnetic radiation, a first reflecting means, a triangular shaped prism, a second reflective means and a detector. In use a beam of electromagnetic radiation from said spectroscopic source thereof is caused to reflect from said first reflective means and enter said triangular shaped prism through a first surface along a normal thereto, reflect from a second surface thereof, the plane of which second surface is oriented substantially horizontally, exit through a third surface thereof along a normal thereto, reflect from said second reflective means and enter said detector. When a fluid or solid sample is caused to be present on said second surface of said prism and said source of spectroscopic electromagnetic radiation is caused to provide a polarized beam of electromagnetic radiation directed toward said first reflective means, the sample affects the reflection characteristics of said second surface of said triangular shaped prism, and analyzing data provided by said detector enables parameters which characterize said fluid or solid to be evaluated.

Another recitation of a method of investigating a fluid or solid sample comprises the steps of providing a source of spectroscopic electromagnetic radiation, a first reflecting means, a trapezoid shaped element, a second reflective means and a detector. In use a beam of electromagnetic radiation from said spectroscopic source thereof is caused to reflect from said first reflective means and enter said trapezoidal shaped element through a first surface along a normal thereto, then at least once:
  reflect from an upper surface thereof, the plane of which upper surface is oriented substantially horizontally, then reflect a lower surface thereof, the plane of which lower surface is oriented substantially horizontally, then again reflect from said upper surface;
and then exit through a second surface thereof along a normal thereto, reflect from said second reflective means and enter said detector. When a fluid or solid is caused to be present on at least one selection from the group consisting of:
  said upper surface of said element; and
  said lower surface of said element;
and said source of spectroscopic electromagnetic radiation is caused to provide a polarized beam of electromagnetic radiation directed toward said first reflective means, the sample affects the reflection characteristics of said second surface of said triangular shaped prism, and analyzing data provided by said detector enables parameters which characterize said fluid or solid to be evaluated.

Yet another recitation of a present invention method of investigating a fluid or solid sample, comprises the steps of providing a source of spectroscopic electromagnetic radiation, an elongated substantially rectangular shaped element which comprises a cut-out portion in a lower elongated surface thereof. In use a beam of electromagnetic radiation from said spectroscopic source thereof is caused to enter a first side of said elongated substantially rectangular shaped element along a normal thereto, reflect from a first side of said cut-out portion in a lower elongated surface thereof to an upper elongated surface thereof, reflect from said upper elongated surface to a second surface of said cut-out portion in said lower elongated surface and exit through a second surface along a normal thereto, the plane of which upper elongated surface is oriented substantially horizontally, then exit through a third surface thereof along a normal thereto, and enter said detector. When fluid or solid is caused to be present on said upper elongated surface of said element and said source of spectroscopic electromagnetic radiation is caused to provide a polarized beam of electromagnetic radiation directed toward said first side of said elongated substantially rectangular shaped element, the sample affects the reflection characteristics of said second surface of said triangular shaped prism, and analyzing data provided by said detector enables parameters which characterize said fluid or solid to be evaluated.

The present invention includes an article of manufacture with an upward facing surface and left and right sides which project substantially vertically downward from left and right sides of said upward facing surface, respectively, and a downward facing surface which centrally comprises a cut-out portion comprising upward to the right and upward to the left directed sides which are mirror images of one another taken about a central vertical plane. In use, a beam of electromagnetic radiation can then be caused to enter said left or right side which projects substantially vertically downward from left and right sides of said upward facing surface, respectively, along a locus which is substantially normal thereto, impinge on said upward to the left or upward to the right directed sides of said cut-out in said downward facing surface, respectively, reflect internally from said upward facing surface then reflect from said upward to the right or upward to the left directed sides of said cut-out in said downward facing surface, respectively, then pass through said right or left side which projects substantially vertically downward from right and left sides which project substantially vertically downward from right and left sides of said upward facing surface, respectively, along a locus which is substantially normal thereto, and proceed out of said article of manufacture.

Continuing, a present invention spectroscopic ellipsometer or polarimeter system can be recited as comprising:
- a polarization state generator for providing a spectroscopic beam of electromagnetic radiation in a known state of polarization;
- a first mirror;
- a substantially triangular shaped prism comprising an upward facing surface and an apex located centrally therebeneath from which first and second sides project upwardly to the left and right to the point that they meet said upward facing surface;
- a second mirror; and
- a polarization state detector for analyzing a spectroscopic beam of electromagnetic radiation.

Said components are oriented such that a beam of spectroscopic electromagnetic radiation provided by said polarization state generator is caused to impinge on said first or second mirror and is directed thereby to enter said first or second side, respectively, of said substantially triangular shaped prism along a locus which is normal thereto, reflect internally from said upward facing surface and exit said second or first side, respectively, of said substantially triangular shaped prism along a locus which is substantially normal thereto, then reflect from said second or first mirror, respectively and proceed into said polarization state detector.

A method of investigation optical properties of a liquid or solid sample then comprises the steps of:
a) providing a spectroscopic ellipsometer or polarimeter system as just described:
b) causing said polarization state generator to provide a beam of electromagnetic radiation which is directed to impinge on said first or second mirror, be directed thereby to enter said first or second side, respectively, of said substantially triangular shaped prism along a locus which is substantially normal thereto, reflect internally from said upward facing surface and exit said second or first side, respectively, of said substantially triangular shaped prism along a locus which is substantially normal thereto, then reflect from said second or first mirror, respectively, and proceed into said polarization state detector, then causing said polarization state detector to output data;
c) causing liquid or solid sample to be present on the upward facing surface of said substantially triangular shaped prism and repeating step b;
d) comparing the polarization state detector output data results obtained in steps b and c;
e) from the comparison in step d determining optical properties of said liquid or solid sample caused to be present on the upward facing surface of said substantially triangular shaped prism in step b.

A modified embodiment of a present invention spectroscopic ellipsometer and polarimeter systems comprises:
- a polarization state generator for providing a spectroscopic beam of electromagnetic radiation in a known state of polarization;
- a first mirror;
- a substantially trapezoidal shaped element comprising an upward facing surface and a downward facing surface which are substantially parallel to one another, there being first and second sides between said upward and downward facing surfaces that project upwardly to the left and right;
- a second mirror; and
- a polarization state detector for analyzing a spectroscopic beam of electromagnetic radiation.

Said components are oriented such that a beam of spectroscopic electromagnetic radiation provided by said polarization state generator is caused to impinge on said first or second mirror and be directed thereby to enter said first or second side of said substantially trapezoidal shaped element, respectively, along a locus which is substantially normal thereto, reflect internally from said upward facing surface at least twice and from said downward facing surface at least once and exit said second or first side, respectively, of said substantially trapezoidal shaped element along a locus which is substantially normal thereto, then reflect from said second or first mirror, respectively and proceed into said polarization state detector.

A method of investigation optical properties of a liquid or solid sample then comprises the steps of:
a) providing a spectroscopic ellipsometer or polarimeter system as just described above:
b) causing said polarization state generator to provide a beam of electromagnetic radiation which is directed to impinge on said first or second mirror, be directed thereby to enter said first or second side, of said substantially trapezoidal shaped element along a locus which is substantially normal thereto, reflect internally from said upward facing surface at least twice and from said downward facing element at least once and exit said second or first side, respectively, of said substantially trapezoidal shaped element along a locus which is substantially normal thereto, then reflect from said second or first mirror, respectively, and proceed into said polarization state detector, then causing said polarization state detector to output data;
c) causing liquid or solid sample to be present on the upward facing surface of said substantially trapezoidal shaped element and repeating step b;
d) comparing the polarization state detector output data results obtained in steps b and c;
e) from the comparison in step d determining optical properties of said liquid or solid sample caused to be present on the upward facing surface of said substantially triangular shaped prism in step b.

Said method can further comprises causing a liquid or solid to be present on the downward facing surface of said trapezoidal shaped element, said liquid or solid being selected from the groups consisting of:
  being the same liquid or solid as placed on the upward facing surface; and
  being a different liquid or solid than that placed on the upward facing surface;

and in which said method further comprises determining properties of said liquid or solid which is caused to be present on the downward facing surface of said trapezoidal shaped element.

Another modified embodiment of a present invention spectroscopic ellipsometer or polarimeter system comprises:
  a polarization state generator for providing a spectroscopic beam of electromagnetic radiation in a known state of polarization;
  an element with an upward facing surface and left and right sides which project substantially vertically downward from left and right sides thereof, respectively, and a downward facing surface which centrally comprises a cut-out portion comprising upward to the right and upward to the left directed sides which are mirror images of one another taken about a vertical plane; and
  a polarization state detector for analyzing a spectroscopic beam of electromagnetic radiation;
which are oriented such that a beam of spectroscopic electromagnetic radiation provided by said polarization state generator is caused to enter said left or right side which projects substantially vertically downward from left and right sides of said upward facing surface, respectively, along a locus which is substantially normal thereto, impinge on said upward to the left or upward to the right directed sides of said cavity in said downward facing surface, respectively, reflect internally from said upward facing surface then reflect from said upward to the right or upward to the left directed sides of said cavity in said downward facing surface, respectively, then pass through said right or left side which projects substantially vertically downward from right and left sides which project substantially vertically downward from right and left sides of said upward facing surface, respectively, along a locus which is substantially normal thereto, and proceed into said polarization state detector.

A method of investigation optical properties of a liquid or solid sample then comprises:
  a) providing a spectroscopic ellipsometer or polarimeter system as just described above:
  b) causing said polarization state generator to provide a beam of electromagnetic radiation which is directed to enter said left or right side which projects substantially vertically downward from left and right sides of said upward facing surface, respectively, along a locus which is substantially normal thereto, impinge on said upward to the left or upward to the right directed sides of said cavity in said downward facing surface, respectively, reflect internally from said upward facing surface then reflect from said upward to the right or upward to the left directed sides of said cavity in said downward facing surface, respectively, then pass through said right or left side which projects substantially vertically downward from right and left sides which project substantially vertically downward from right and left sides of said upward facing surface, respectively, along a locus which is substantially normal thereto, and proceed into said polarization state detector;
  c) causing liquid or solid sample to be present on the upward facing surface of said element with an upward facing surface and left and right sides which project substantially vertically downward from left and right sides thereof, respectively, and a downward facing surface which centrally comprises a cut-out portion comprising upward to the right and upward to the left directed sides which are mirror images of one another taken about a vertical plane substantially triangular shaped prism and repeating step b;
  d) comparing the polarization state detector output data results obtained in steps b and c;
  e) from the comparison in step d determining optical properties of said liquid or solid sample caused to be present on the upward facing surface of said element with an upward facing surface and left and right sides which project substantially vertically downward from left and right sides thereof, respectively, and a downward facing surface which centrally comprises a cut-out portion comprising upward to the right and upward to the left directed sides which are mirror images of one another taken about a vertical plane.

The present invention will be better understood by reference to the detailed description Section of this Specification, in conjunction with the Drawings.

DETAILED DESCRIPTION

Figure 1:
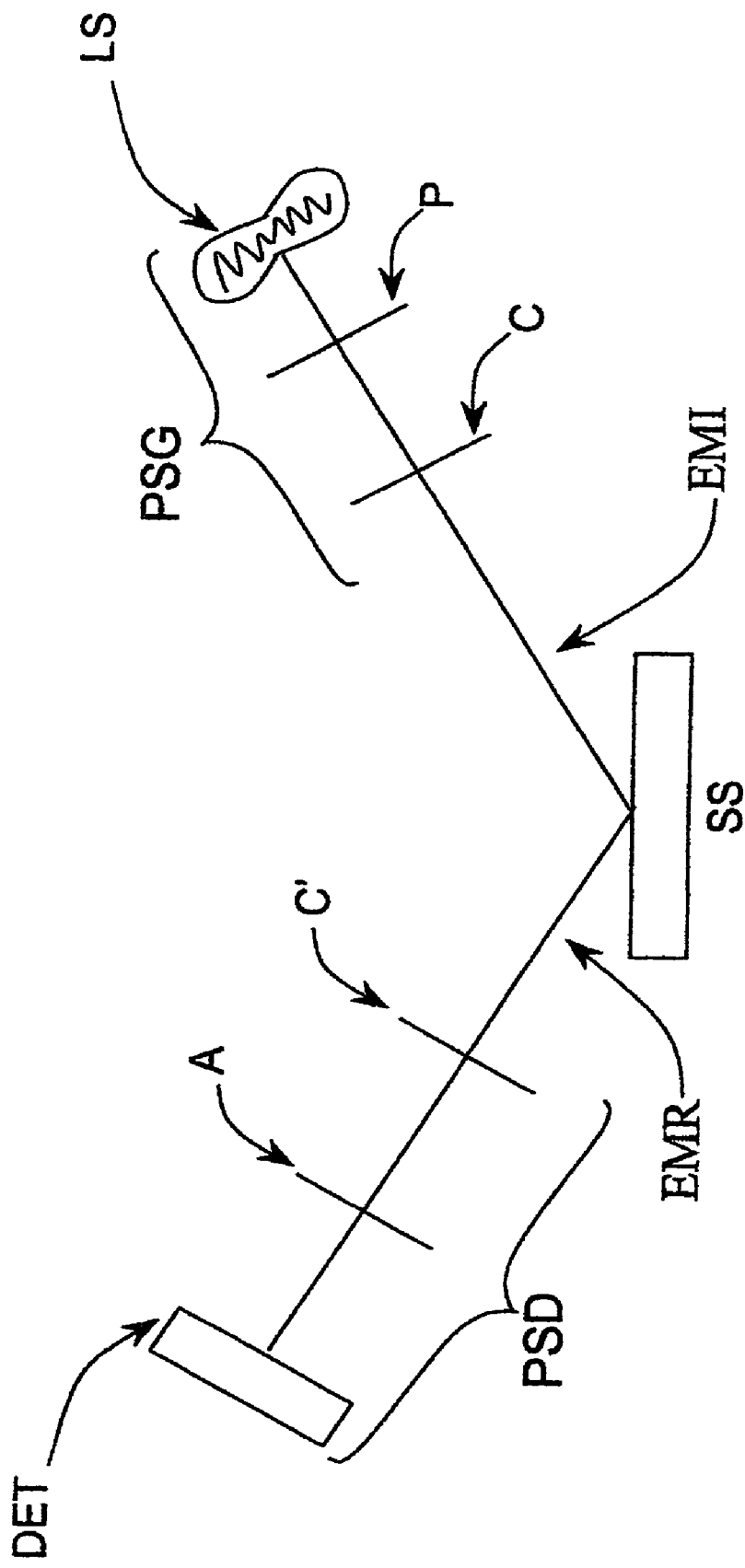
FIG. 1 shows a prior art ellipsometer or polarimeter system.

Turning now to the Drawings, there is shown in FIG. 1, a prior art Ellipsometer or Polarimeter system which is comprised of a Polarization State Generator (PSG) and Polarization State Detector (PSD). The Polarization State Generator (PSG) is shown as comprising a Source (LS) of a Beam of Electromagnetic Radiation (EMI) which is caused to be in a State of Polarization by passage through a Polarizer (P) and optionally a Compensator (C) before impinging on a Sample (SS) at an oblique angle of incidence. The Polarization State Detector (PSD) is shown as comprising an optional Compensator (C'), and Analyzer (A) and a Detector (DET). For insight, the FIG. 1 system is typically considered to be an Ellipsometer when the optional Compensators are not present, and to be a Polarimeter when at least one Compensator (C) or (C') is present.

Figure 2:
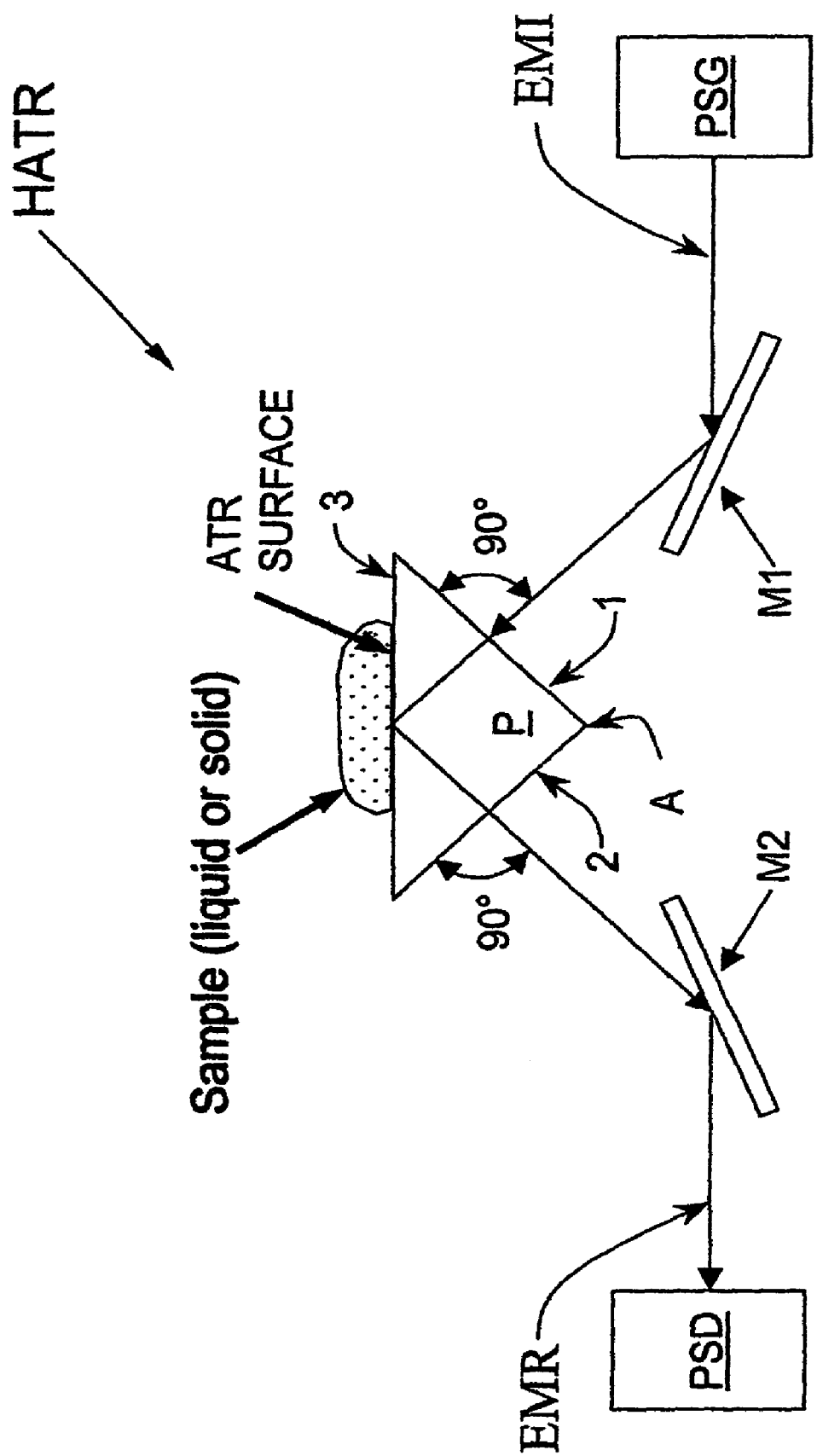
FIGS. 2-4 demonstrate variously embodied present invention Horizontal Attenuated Total Reflection (HATR) systems in the context of Spectroscopic Ellipsometer or Polarimeter systems which comprise a Polarization State Generator (PSG) and a Polarization State Detector (PSD).
Figure 3:
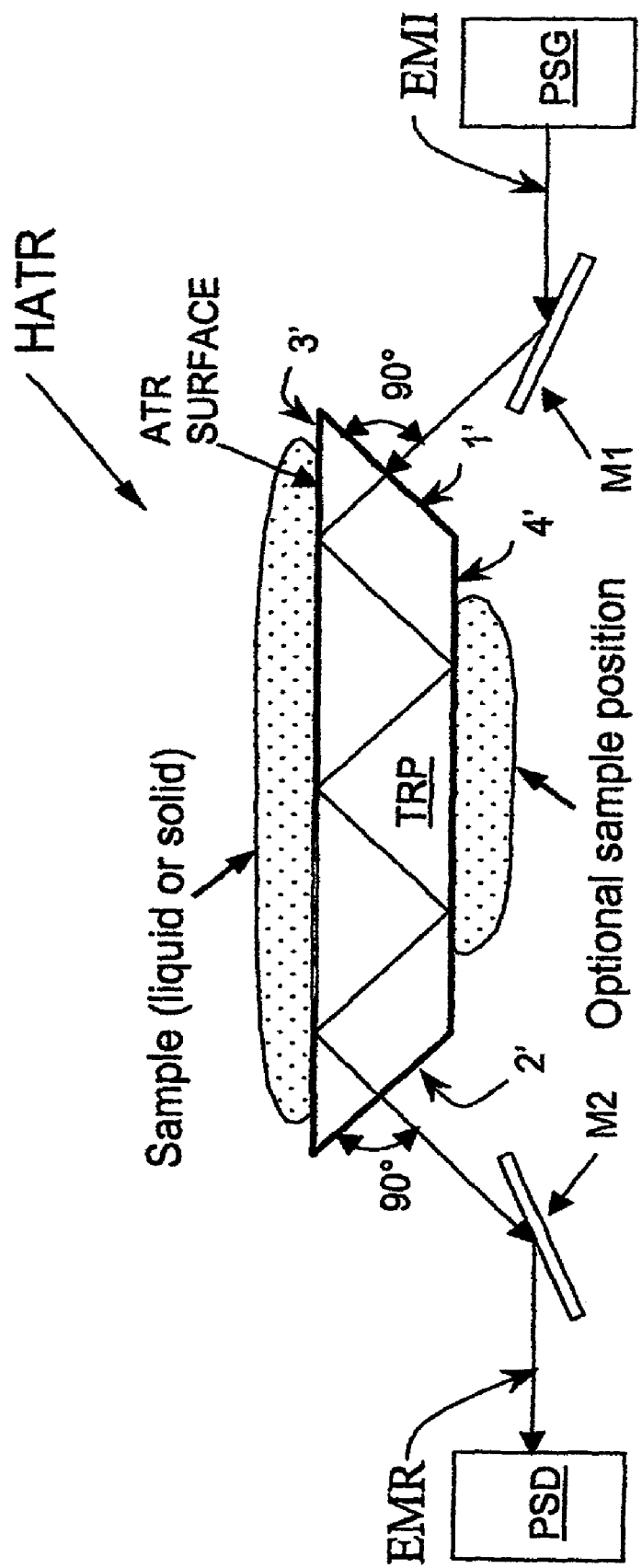
Figure 4:
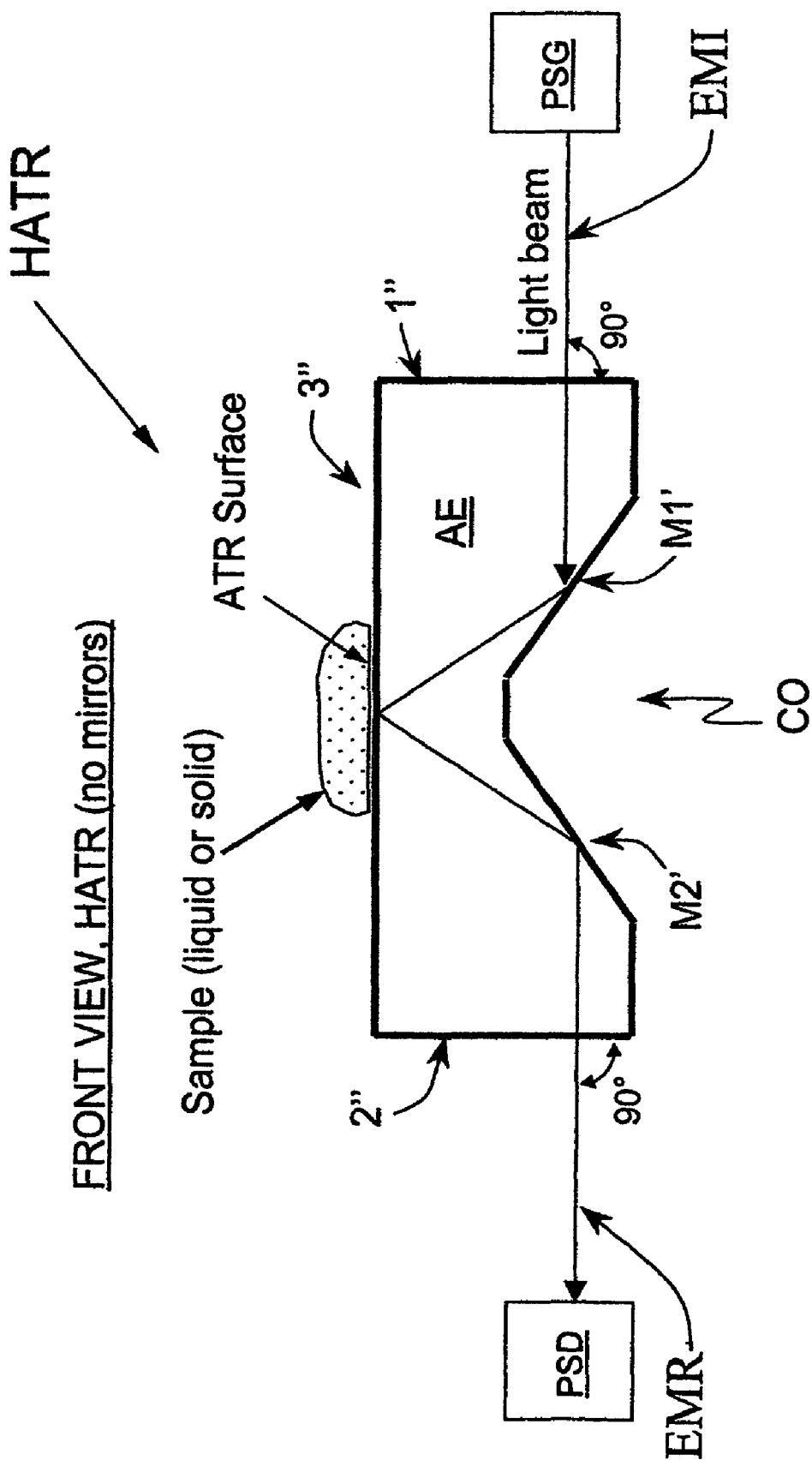

Continuing, FIGS. 2-4 demonstrate various embodiments of a present invention Horizontal Attenuated Total Reflection (HATR) system in the context of a Spectroscopic Ellipsometer or Polarimeter system, which as indicated by FIG. 1, is comprised of a Polarization State Generator (PSG) and Polarization State Detector (PSD). Note however, that the Sample (SS) of FIG. 1 is replaced with a Horizontal Attenuated Total Reflection (HATR) system in FIGS. 2-4.

As regards FIG. 2, there is shown a Polarization State Generator (PSG) which provides a Polarized Beam of Electromagnetic Radiation (EMI) to a first Mirror (M1), which in turn reflects it to enter a substantially triangular shaped Prism (P) comprising an upward facing Surface (3) and an Apex (A) located centrally therebeneath from which First (1) and Second (2) sides project upwardly to the left and right to the point that they meet said upward facing Surface (3). Note that the electromagnetic beam enters the First side (1) of said substantially triangular shaped Prism (P) along a locus which is substantially normal thereto, then reflects internally from said upward facing surface and exits said Second side (2), of said substantially triangular shaped Prism (P) along a locus which is substantially normal thereto. The electromagnetic beam then reflects from said Second mirror (M2) and proceeds into said Polarization State Detector (PSD).

Note that a Solid or liquid Sample is shown present atop the upward facing Surface (3), and its presence serves to modify the internal reflecting properties of said upward facing Surface (3). As indicated in the Disclosure of the Invention Section herein, determination of the change in internal reflection properties of the upward facing Surface (3) as a result of the presence of the Sample can provide insight to optical properties of said Sample. It is also mentioned that the location of the (PSG) and (PSD) can be switched so that the (PSG) provides a beam of electromagnetic radiation to the Second Mirror (M2) and the beam reflected from the First Mirror (M1) enters the (PSD) without otherwise changing the operation of the (HATR) system.

FIG. 3 shows a Polarization State Generator (PSG) which provides a Polarized Beam of Electromagnetic Radiation (EMI) to a first Mirror (M1), which in turn reflects it to enter a substantially trapezoidal shaped element comprising an upward facing surface and a shorter downward facing surface which are substantially parallel to one another, there being first and second sides between said upward and downward facing surfaces that project respectively upwardly to the left and right. Note that the electromagnetic beam enters the First side (1') of said substantially trapezoidal shaped element (TRP) along a locus which is substantially normal thereto, then reflects internally from said upward facing surface at least twice and from said downward facing surface at least once and then exit said Second side (2') of said substantially trapezoidal shaped element along a locus which is substantially normal thereto, then reflect from said Second Mirror (M2) and proceed into said Polarization State Detector (PSD). It is again mentioned that the location of the (PSG) and (PSD) can be switched so that the (PSG) provides a beam of electromagnetic radiation to the Second Mirror (M2) and the beam reflected from the First Mirror (M1) enters the (PSD) without otherwise changing the operation of the (HATR) system. Note that sample is placed on the Upward Facing Surface (3') and its presence changes the internal reflective properties of said Upward Facing Surface (3'). In addition, in the FIG. 3 embodiment sample can optionally be placed on the Downward Facing Surface (4') as shown, which sample on said Downward Facing Surface (4') can be the same or different from that on the Upward Facing Surface (3').

FIG. 4 shows a Polarization State Generator (PSG) which, provides a Polarized Beam of Electromagnetic Radiation (EMI) to a an Element (AE) with an Upward Facing Surface (3") and Left (2") and Right (1") sides which project substantially vertically downward from left and right sides of said Upward Facing Surface (3"), and further comprises a Downward Facing Surface which centrally comprises a Cut-out (CO) portion comprising Upward to the Right (M1') and Upward to the Left (M2') directed sides which are mirror images of one another taken about a central vertical plane. In use said Polarization State Generator (PSG) provides a Beam of Electromagnetic Radiation (EMI) which is directed to enter said Right side (1") which projects substantially vertically downward from the Right side of said upward facing surface (3"), along a locus which is substantially normal thereto, then impinge on said Upward to the Left (1"') directed side of said Cut-out (CO) in said Downward Facing Surface, reflect internally from said Upward Facing Surface (3") and then reflect from said Upward to the Right (M2') directed side of said Cut-out (CO) in said Downward Facing Surface, and then pass through said Left side (2") which projects substantially vertically downward from the left side which project substantially vertically downward from the left side of said Upward Facing Surface (3") along a locus which is substantially normal thereto, and proceed into said Polarization State Detector (PSD). It is again mentioned that the location of the (PSG) and (PSD) can be switched so that the (PSG) provides a beam of electromagnetic radiation to the Left side (2") which projects substantially vertically downward from the left side which project substantially vertically downward from the left side of said Upward Facing Surface (3"), and the beam reflected from the Upward to the Right projecting side (M1') of the Cut-out (CO) enters the (PSD), without otherwise changing the operation of the (HATR) system. Note that a Solid or liquid Sample is shown present atop the upward facing Surface (3"), and its presence serves to modify the internal reflecting properties of said upward facing Surface (3"). Note that a Solid or liquid Sample is shown present atop the Upward Facing Surface (3"), and its presence serves to modify the internal reflecting properties of said upward facing Surface (3").

It is to be understood that the terminology "fluid" and "liquid" are to be considered essentially equivalent herein. The distinction being that a liquid is typically flowable at room temperature and remains so over time, whereas a fluid might be "flowable" at other than room temperature, or might be flowable at room temperature but cease to be flowable after some time period, rather than remain flowable as a liquid.

Finally, it is to be understood that FIGS. 2-4 are shown in elevation and described as such. While the orientation resulting from a 90 degree rotation is excluded, said description does not limit application of the systems shown when they are rotated 180 degrees, so the what has been referred to as upward and downward are oriented to face downward and upward, respectively.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

I claim:

1. A spectroscopic ellipsometer or polarimeter system comprising:
   a polarization state generator for providing a spectroscopic beam of electromagnetic radiation in a known state of polarization;
   an element with an upward facing surface and left and right sides which project substantially vertically downward from left and right sides of said upward facing surface, respectively, and a downward facing surface which centrally comprises a cut-out portion comprising upward to the right and upward to the left directed sides surfaces which are mirror images of one another taken about a central vertical plane; and
   a polarization state detector for analyzing a spectroscopic beam of electromagnetic radiation;
   said spectroscopic ellipsometer or polarimeter system being configured such that a beam of spectroscopic electromagnetic radiation provided by said polarization state generator is caused to enter said left or right side which projects substantially vertically downward from left and right sides of said upward facing surface, respectively, along a locus which is substantially normal thereto, impinge on said upward to the left or upward to the right directed surfaces of said cut-out in said downward facing surface, respectively, reflect internally from said upward facing surface then reflect from said upward to the right or upward to the left directed surfaces of said cut-out in said downward facing surface, respectively, then pass through said right or left side which projects substantially vertically downward from right and left sides which project substantially vertically downward from right and left sides of said upward facing surface, respectively, along a locus which is substantially normal thereto, and proceed into said polarization state detector.

2. A spectroscopic ellipsometer or polarimeter system as in claim 1, which is rotated 180 degrees about a horizontal axis.

3. A method of investigation optical properties of a liquid or solid sample comprising the steps of:
  a) providing a spectroscopic ellipsometer or polarimeter system comprising:
    a polarization state generator for providing a spectroscopic beam of electromagnetic radiation in a known state of polarization;
    an element with an upward facing surface and left and right sides which project substantially vertically downward from left and right sides thereof, respectively, and a downward facing surface which centrally comprises a cut-out portion comprising upward to the right and upward to the left directed surfaces which are mirror images of one another taken about a vertical plane; and
    a polarization state detector for analyzing a spectroscopic beam of electromagnetic radiation;
    said spectroscopic ellipsometer or polarimeter system being configured such that a beam of spectroscopic electromagnetic radiation provided by said polarization state generator is caused to enter said left or right side which projects substantially vertically downward from left and right sides of said upward facing surface, respectively, along a locus which is substantially normal thereto, impinge on said upward to the left or upward to the right directed surfaces of said cut-out in said downward facing surface, respectively, reflect internally from said upward facing surface then reflect from said upward to the right or upward to the left directed surfaces of said cut-out in said downward facing surface, respectively, then pass through said right or left side which projects substantially vertically downward from right and left sides which project substantially vertically downward from right and left sides of said upward facing surface, respectively, along a locus which is substantially normal thereto, and proceed into said polarization state detector;
  b) operating said polarization state generator so that it provides a beam of electromagnetic radiation which is directed to enter said left or right side which projects substantially vertically downward from left and right sides of said upward facing surface, respectively, along a locus which is substantially normal thereto, impinge on said upward to the left or upward to the right directed sides of said cut-out in said downward facing surface, respectively, reflect internally from said upward facing surface then reflect from said upward to the right or upward to the left directed sides of said cut-out in said downward facing surface, respectively, then pass through said right or left side which projects substantially vertically downward from right and left sides which project substantially vertically downward from right and left sides of said upward facing surface, respectively, along a locus which is substantially normal thereto, and proceed into said polarization state detector;
  c) placing liquid or solid sample on the upward facing surface of said element with an upward facing surface and left and right sides which project substantially vertically downward from left and right sides thereof, respectively, and a downward facing surface which centrally comprises a cut-out portion comprising upward to the right and upward to the left directed sides which are mirror images of one another taken about a vertical plane substantially triangular shaped prism and operating said polarization state generator so that it provides a beam of electromagnetic radiation which is directed to enter said left or right side which projects substantially vertically downward from left and right sides of said-upward facing surface, respectively, along a locus which is substantially normal thereto, impinge on said upward to the left or upward to the right directed sides of said cut-out in said downward facing surface, respectively, reflect internally from said upward facing surface then reflect from said upward to the right or upward to the left directed sides of said cut-out in said downward facing surface, respectively, then pass through said right or left side which projects substantially vertically downward from right and left sides which project substantially vertically downward from right and left sides of said upward facing surface, respectively, along a locus which is substantially normal thereto, and proceed into said polarization state detector;
  d) comparing the polarization state detector output data results obtained in step b to that obtained in step c;
  e) from the comparison in step d determining optical properties of said liquid or solid sample caused to be present on the upward facing surface of said element with an upward facing surface and left and right sides which project substantially vertically downward from left and right sides thereof, respectively, and a downward facing surface which centrally comprises a cut-out portion comprising upward to the right and upward to the left directed surfaces which are mirror images of one another taken about a vertical plane.

4. A method as in claim 3, which further comprise the step of rotating said spectroscopic ellipsometer or polarimeter system 180 degrees about a horizontal axis after the provision thereof.

* * * * *